(12) United States Patent
Janke et al.

(10) Patent No.: US 6,501,994 B1
(45) Date of Patent: Dec. 31, 2002

(54) HIGH IMPEDANCE ELECTRODE TIP (75) Inventors: Aaron W. Janke, St. Paul, MN (US);
Mary Lee Cole, St. Paul, MN (US);
Ronald W. Heil, Jr., Roseville, MN (US); Jeffrey T. Bartig, Maplewood, MN (US); Gary W Goebel, Vadnais Heights, MN (US); Douglas A Heitkamp, White Bear Lake, MN (US); Randall M. Peterfeso, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/121,288

(22) Filed: Jul. 22, 1998

Related U.S. Application Data (63) Continuation-in-part of application No. 08/998,174, filed on Dec. 24, 1997, now abandoned.

(51) Int. Cl.[7] .................................................. A61N 1/05
(52) U.S. Cl. ...................................................... 607/127
(58) Field of Search ................................ 607/126–131, 607/121

(56) References Cited

U.S. PATENT DOCUMENTS

| | | | |
|---|---|---|---|
| 3,614,955 A | | 10/1971 | Mirowski |
| 3,804,098 A | | 4/1974 | Friedman |
| 3,911,928 A | * | 10/1975 | Lagergren .................... 607/122 |
| 3,942,536 A | | 3/1976 | Mirowski et al. |
| 4,010,758 A | * | 3/1977 | Rockland et al. ............ 607/131 |
| 4,026,303 A | * | 5/1977 | Babotai ........................ 607/126 |
| 4,030,508 A | | 6/1977 | Thalen |

(List continued on next page.)

FOREIGN PATENT DOCUMENTS

| | | | |
|---|---|---|---|
| EP | 0 42551 | 6/1980 | ............. A61N/1/04 |
| EP | 0042551 | * 12/1981 | .................. 607/126 |
| EP | 0057877 | 8/1982 | .................. 607/121 |

(List continued on next page.)

OTHER PUBLICATIONS

Fain, et al., "A New Internal Defibrillation Lead System: Intrapericardial Placement Without Thoracotomy", Abstracts Circulation, 76, Suppl. IV, 1839 (Oct. 1987).
Jones, D.L., et al., "Internal Cardiac Defibrillation in Man: Pronounced Improvement with Sequential Pulse Delivery to Two Different Lead Orientations", *Circulation*, vol. 73, No. 3, p. 484–491 (Mar. 1986).

*Primary Examiner*—George R. Evanisko
(74) *Attorney, Agent, or Firm*—Schwegman, Lundberg, Woessner & Kluth P.A.

(57) ABSTRACT

An implantable lead, being either a fixed or retractable/extendable lead, having a distal tip electrode is adapted for implantation on or about the heart and for connection to a system for monitoring or stimulating cardiac activity. The electrode includes a mechanical fastener such as a fixation helix for securing the electrode to cardiac tissue, which may or may not be electrically active. The implantable electrode with a helical tip includes an electrode which has a distal end and a proximal end. A helix is disposed within the electrode, where the helix is aligned along a radial axis of the electrode. The electrode further includes one or more of the following features: the helix having a coating of an insulating material on a surface of the helix, a porous conductive surface at a base of the helix, a porous conductive element at the end of the electrode having an insulating coating covering from 5–95% of the surface of the porous conductive element. The electrode may farther include an electrode tip having a porous electrical conductive element, such as a mesh screen, disposed on a surface at the distal end of the electrode tip, which can be used as a sensing or pacing interface with the cardiac tissue.

16 Claims, 6 Drawing Sheets

U.S. PATENT DOCUMENTS

| | | | |
|---|---|---|---|
| 4,030,509 A | 6/1977 | Heilman et al. | |
| 4,106,512 A | 8/1978 | Bisping | |
| 4,136,703 A | 1/1979 | Wittkampf | |
| 4,217,913 A | 8/1980 | Dutcher | |
| 4,270,549 A | 6/1981 | Heilman | |
| 4,291,707 A | 9/1981 | Heilman et al. | |
| 4,311,153 A | 1/1982 | Smits | |
| 4,437,474 A | 3/1984 | Peers-Trevarton | |
| 4,458,695 A | 7/1984 | Peers-Trevarton | |
| 4,463,765 A | 8/1984 | Gold | |
| 4,469,104 A | 9/1984 | Peers-Trevarton | |
| 4,548,203 A | 10/1985 | Tacker, Jr. et al. | |
| 4,559,951 A | 12/1985 | Dahl et al. | |
| 4,567,900 A | 2/1986 | Moore | |
| 4,570,642 A | 2/1986 | Kane et al. | |
| 4,603,705 A | 8/1986 | Speicher et al. | |
| 4,624,265 A | 11/1986 | Grassi | |
| 4,624,266 A | 11/1986 | Kane | |
| 4,627,439 A | 12/1986 | Harris | |
| 4,633,880 A | 1/1987 | Osypka et al. | |
| 4,646,755 A | 3/1987 | Kane | |
| 4,649,937 A | 3/1987 | DeHaan et al. | |
| 4,649,938 A | 3/1987 | McArthur | |
| 4,662,377 A | 5/1987 | Heilman et al. | |
| 4,662,382 A * | 5/1987 | Sluetz et al. | 607/126 |
| 4,664,113 A | 5/1987 | Frisbie et al. | |
| 4,727,877 A | 3/1988 | Kallok | |
| 4,784,161 A | 11/1988 | Skalsky et al. | |
| 4,799,486 A | 1/1989 | DuFault | |
| 4,799,493 A | 1/1989 | DuFault | |
| 4,817,608 A | 4/1989 | Shapland et al. | |
| 4,817,634 A | 4/1989 | Holleman et al. | |
| 4,819,647 A | 4/1989 | Byers et al. | |
| 4,819,661 A * | 4/1989 | Heil, Jr. et al. | |
| 4,819,662 A | 4/1989 | Heil, Jr. et al. | |
| 4,827,932 A | 5/1989 | Ideker et al. | |
| 4,860,769 A | 8/1989 | Fogarty et al. | |
| 4,865,037 A | 9/1989 | Chin et al. | |
| 4,886,074 A | 12/1989 | Bisping | |
| 4,905,691 A | 3/1990 | Rydell | |
| 4,924,881 A | 5/1990 | Brewer | |
| 4,938,231 A | 7/1990 | Milijasevic et al. | |
| 4,944,300 A | 7/1990 | Saksena | |
| 4,953,551 A | 9/1990 | Mehra et al. | |
| 4,953,564 A | 9/1990 | Berthelsen | |
| 4,967,766 A | 11/1990 | Bradshaw | |
| 4,971,070 A | 11/1990 | Holleman et al. | |
| 4,998,975 A | 3/1991 | Cohen et al. | |
| 5,002,067 A | 3/1991 | Berthelsen et al. | |
| 5,016,645 A | 5/1991 | Williams et al. | |
| 5,016,646 A | 5/1991 | Gotthardt et al. | |
| 5,016,808 A | 5/1991 | Heil, Jr. et al. | |
| 5,020,544 A | 6/1991 | Dahl et al. | |
| 5,044,375 A | 9/1991 | Bach, Jr. et al. | |
| 5,050,601 A | 9/1991 | Kupersmith et al. | |
| 5,056,516 A | 10/1991 | Spehr | |
| 5,063,932 A | 11/1991 | Dahl et al. | |
| 5,076,285 A | 12/1991 | Hess et al. | |
| 5,083,562 A | 1/1992 | de Coriolis et al. | |
| 5,105,826 A | 4/1992 | Smits et al. | |
| 5,107,834 A | 4/1992 | Ideker et al. | |
| 5,111,811 A | 5/1992 | Smits | |
| 5,111,812 A | 5/1992 | Swanson et al. | |
| 5,129,404 A | 7/1992 | Spehr et al. | |
| 5,133,353 A | 7/1992 | Hauser | |
| 5,133,365 A | 7/1992 | Heil, Jr. et al. | |
| 5,152,299 A | 10/1992 | Soukup | |
| 5,165,403 A | 11/1992 | Mehra | |
| 5,174,303 A | 12/1992 | Schroeppel | |
| 5,203,348 A | 4/1993 | Dahl et al. | |
| 5,209,229 A | 5/1993 | Gilli | |
| 5,217,028 A * | 6/1993 | Dutcher et al. | 607/127 |
| 5,230,337 A | 7/1993 | Dahl et al. | |
| 5,259,394 A | 11/1993 | Bens | |
| 5,259,395 A | 11/1993 | Li | |
| 5,261,400 A | 11/1993 | Bardy | |
| 5,269,319 A | 12/1993 | Schulte et al. | |
| 5,271,417 A | 12/1993 | Swanson et al. | |
| 5,282,845 A | 2/1994 | Bush et al. | |
| 5,300,108 A | 4/1994 | Rebell et al. | |
| 5,300,110 A | 4/1994 | Latterell et al. | |
| 5,306,292 A * | 4/1994 | Lindegren | 607/11 |
| 5,314,459 A | 5/1994 | Swanson et al. | |
| 5,324,327 A * | 6/1994 | Cohen | 607/122 |
| 5,342,414 A | 8/1994 | Mehra | |
| 5,344,439 A | 9/1994 | Otten | |
| 5,358,516 A | 10/1994 | Myers et al. | |
| 5,366,496 A | 11/1994 | Dahl et al. | |
| 5,374,286 A | 12/1994 | Morris | |
| 5,383,908 A | 1/1995 | Sweeney et al. | |
| 5,397,342 A | 3/1995 | Heil, Jr. et al. | |
| 5,405,373 A * | 4/1995 | Petersson et al. | 607/121 |
| 5,411,544 A | 5/1995 | Mar et al. | |
| 5,425,755 A | 6/1995 | Doan | |
| 5,425,756 A | 6/1995 | Heil, Jr. et al. | |
| 5,447,533 A | 9/1995 | Vachon et al. | |
| 5,447,534 A | 9/1995 | Jammet | |
| 5,456,706 A | 10/1995 | Pless et al. | |
| 5,456,708 A | 10/1995 | Doan et al. | |
| 5,476,501 A | 12/1995 | Stewart et al. | |
| 5,492,119 A | 2/1996 | Abrams | |
| 5,500,008 A | 3/1996 | Fain | |
| 5,515,848 A | 5/1996 | Corbett, III et al. | |
| 5,522,874 A * | 6/1996 | Gates | 607/127 |
| 5,524,338 A | 6/1996 | Martynuik et al. | |
| 5,531,780 A | 7/1996 | Vachon | |
| 5,534,022 A | 7/1996 | Hoffmann et al. | |
| 5,545,201 A * | 8/1996 | Helland et al. | |
| 5,545,205 A | 8/1996 | Schulte et al. | |
| 5,554,178 A | 9/1996 | Dahl et al. | |
| 5,578,068 A | 11/1996 | Laske et al. | |
| 5,654,030 A | 8/1997 | Munshi et al. | |
| 5,709,753 A | 1/1998 | Olson et al. | |
| 5,720,099 A | 2/1998 | Parker et al. | |
| 5,728,140 A * | 3/1998 | Salo et al. | 607/9 |
| 5,837,006 A | 11/1998 | Ocel et al. | |
| 5,871,529 A * | 2/1999 | Bartig et al. | 607/122 |
| 5,871,531 A * | 2/1999 | Struble | |
| 5,925,045 A | 7/1999 | Reimels et al. | |
| 5,935,159 A | 8/1999 | Cross, Jr. et al. | |
| 5,972,416 A | 10/1999 | Reimels et al. | |
| 5,978,705 A | 11/1999 | KenKnight et al. | 607/5 |
| 6,097,986 A * | 8/2000 | Janke et al. | |

FOREIGN PATENT DOCUMENTS

| | | | | |
|---|---|---|---|---|
| EP | 0452278 | 10/1991 | | A61N/1/05 |
| EP | 0460324 | 12/1991 | | A61N/1/05 |
| EP | 0573275 | 12/1993 | | |
| EP | 0612538 | 8/1994 | | A61N/1/05 |
| EP | 0672431 | 9/1995 | | A61N/1/05 |
| GB | 2032278 | 6/1980 | | A61M/25/00 |
| GB | 2240721 | 8/1991 | | |
| WO | 89/06148 | 7/1989 | | A61N/1/05 |
| WO | 92/07616 | 5/1992 | | |

* cited by examiner

HIGH IMPEDANCE ELECTRODE TIP

RELATED APPLICATIONS

This application is a Continuation-in-Part of U.S. patent application Ser. No. 08/998,174, filed Dec. 24, 1997, entitled "RETRACTABLE LEAD WITH MESH SCREEN", now abandoned.

This application is also related to the following co-pending applications:

U.S. patent application Ser. No. 08/992,039, filed Dec. 17, 1997, entitled "RETRACTABLE LEAD WITH MESH SCREEN", and U.S. patent application Ser. No. 09/120,824, filed Jul. 22, 1998, entitled SINGLE PASS LEAD SYSTEM".

BACKGROUND OF THE ART

FIELD OF THE INVENTION

The present invention relates generally to leads for conducting electrical signals to and from the heart. More particularly, it pertains to electrode tips for delivering electrical charges to the heart, and to tips which tend to reduce power consumption from cells without reducing the effective level of each pace.

BACKGROUND OF THE INVENTION

Leads implanted in the body for electrical cardioversion or pacing of the heart are generally known in the art. In particular, electrically transmissive leads may be implanted in or about the heart to reverse (i.e., defibrillate or cardiovert) certain life threatening arrhythmias or to stimulate contraction (pacing) of the heart. Electrical energy is applied to the heart via the leads to return the heart to normal rhythm. Leads have also been used to sense conditions, materials or events (generally referred to as "sense" or "sensing") in the body, such as in the atrium or ventricle of the heart and to deliver pacing pulses to the atrium or ventricle. Tachy leads generally can at least sense, pace, and deliver defibrillation shocks. Brady leads can at least perform the combination functions of pacing and sensing the heart. One of the available functions of the pacemaker or the automatic implantable cardioverter defibrillator (AICD) is to receive signals from a lead and interpret signals. In response to these signals, the pacemaker can decide to pace or not pace. The AICD can decide to pace or not pace, and shock or not shock. In response to a sensed bradycardia or tachycardia condition, a pulse generator produces pacing or defibrillation pulses to correct the condition. The same lead used to sense the condition is sometimes also used in the process of delivering a corrective pulse or signal from the pulse generator of the pacemaker.

Sick sinus syndrome and symptomatic AV (atrial-ventricular) block constitute two of the major reasons for insertion of cardiac pacemakers today. Cardiac pacing may be performed by the transvenous method or by leads implanted directly onto the ventricular epicardium. Most commonly, permanent transvenous pacing is performed using a lead positioned within one or more chambers of the heart. A lead, sometimes referred to as a catheter, may be positioned in the right ventricle or in the right atrium through a subclavian vein or other vascular port, and lead terminal pins are attached to a pacemaker which is implanted subcutaneously. The lead may also be positioned in both chambers, depending on the lead, as when a lead passes through the atrium to the ventricle. Sense electrodes may be positioned within the atrium or the ventricle of the heart as appropriate for the particular condition or the choice of the medical practitioner.

Pacemaker leads represent the electrical link between the pulse generator and the heart tissue which is to be excited. These pacemaker leads include single or multiconductor coils of insulated wire having an insulating sheath. The coils provide a cylindrical envelope or tube, many times referred to as a lumen, which provides a space into which a stiffening stylet can be inserted. The conductive coil is connected to an electrode in an electrode assembly at a distal end of a pacing lead. Typically, a terminal member is molded within a flexure sleeve at the proximal end of the pacing lead and connected to the proximal end of the conductive coil.

After the electrode assembly is positioned at a desired location within the heart, it is desirable to provide some method for securing the electrode assembly at that location. Mechanical fixation devices are used to firmly anchor the electrodes in the heart. One type of mechanical fixation device used is a corkscrew, or a helix electrode connector. During placement of the lead, the tip of the lead travels intravenously through veins and the heart. While traveling through the veins, the helix electrode connector at the tip of the lead may snag or attach to the side wall of the vein. Since this is highly undesirable as it may cause damage or other complications to a patient, retractable helixes are one of the optional constructions which have been provided for leads. In addition, temporary caps over the helix (such as an aqueous soluble cap, particularly a water soluble, innocuous organic material such as a sugar, starch or other biologically inert, or digestible material such as sugars, starches and the like (e.g., mannitol, sorbitol) may be formed over the helix or tip. Preferably these materials are at least soluble or dispersible and preferably are inert or even digestible.

When using a retractable helix, the helix is extended and screwed into the heart muscle by applying a torque to the other end of the conductor without use of any further auxiliary device or with a special fixation stylet. A fixed or non-retractable helix electrode connector needs only to be positioned and secured to the heart muscle by the application of torque. If a soluble/dispersible cap is present on the helix, the cap must be given sufficient time to dissolve or disperse before complete securement of the helix electrode connector is attempted. A lead must be capable of being firmly secured into the wall of the cardiac tissue to prevent dislodgement therefrom, while avoiding perforation of the electrode completely through the cardiac tissue.

The pulse generator circuitry and power supply work in concert with the electrodes as a system which provides electrical pulses to the heart tissue. A low impedance electrode design may increase power delivery to the heart tissue, but at the same time, this higher energy usage results in shorter battery life. Shorter battery life is undesirable, since it increases the average number of surgical procedures to perform battery replacement for a patient.

There is a need for a body-implantable lead that has a helix for fixation to the wall of the atrium or ventricle of the heart. A separate desirable feature in body-implantable leads is for a lead having an electrode for positioning within the atrium or ventricle that allows for tissue ingrowth. Tissue ingrowth further enhances the electrical performance of the lead. The lead and electrode are further stabilized within the heart as a result of tissue ingrowth. Furthermore, there is a need for a relatively high pacing impedance electrode design which offers reasonable average voltage threshold with sufficient signal amplitude so that the pacing function would be effectively provided with reduced energy utilization and consequently extend battery life.

SUMMARY OF THE INVENTION

According to the present invention, there is provided a body-implantable lead assembly comprising a lead, one end of the lead being adapted to be connected to electrical supply for providing or receiving electrical pulses. The other end of the lead comprises a distal tip which is adapted to be connected to tissue of a living body. The lead is characterized by having either a) a porous electrode at the base of the helix and/or b) an insulating coating over a portion of the helix so that the impedance is increased for the helix as compared to a helix of the same size and materials without an insulating coating. The lead also has an increased impedance or high impedance which can act to extend the life of the battery. The high or at least the increased impedance may be effected in any of a number of ways, including, but not limited to one or more of the following structures: 1) a fully insulated tissue-engaging tip with an electrode at the base of the insulated tip, 2) a partially insulated engaging tip (only a portion of the surface area of the engaging tip being insulated), 3) a mesh or screen of material at the distal end of the lead, at the base of an extended engaging tip (whether a fixed or retractable tip), 4) the selection of materials in the composition of the mesh and/or tip which provide higher impedance, 5) the partial insulative coating of a mesh or screen to increase its pacing impedance, and 6) combinations of any of these features. There may be various constructions to effect the high impedance, including the use of helical tips with smaller surface areas (e.g., somewhat shorter or thinner tips). There may also be a sheath of material inert to body materials and fluids and at least one conductor extending through the lead body. The use of these various constructions in the tip also allows for providing the discharge from the tip in a more highly resolved location or area in the tip.

According to the present invention, there is provided a body-implantable lead assembly comprising a lead, one end being adapted to be connected to electrical supply for providing or receiving electrical pulses. The lead further comprises a distal tip which is adapted to be connected to tissue of a living body. The lead also has a high impedance to extend the life of the battery. There may be various constructions to effect the high impedance function. There may also be a sheath of material at the distal end of the lead assembly, with the sheath being inert to body materials and fluids and at least one conductor extending through the lead body.

The distal tip electrode is adapted, for example, for implantation proximate to the heart while connected with a system for monitoring or stimulating cardiac activity. The distal tip electrode includes an electrode tip (preferably with only a percentage of its entire surface area being electrically conductively exposed —only a portion of the surface is insulated—to increase its impedance), preferably a mesh screen disposed at a distal end of the electrode tip, a fixation helix disposed within the electrode tip, and a helix guiding mechanism. The mesh screen preferably is electrically active, and the area of the mesh screen and the percentage of electrically exposed surface area of the electrode tip can be changed to control electrical properties. Further, the mesh screen can entirely cover an end surface of the electrode tip, or a portion of the end surface in the form of an annular ring. In one embodiment, the helix guiding mechanism includes a hole punctured within the mesh screen. Alternatively, the helix guiding mechanism can include a guiding bar disposed transverse to a radial axis of the electrode. The helix is retractable, and is in contact with a movement mechanism. The movement mechanism provides for retracting the helix, such as during travel of the electrode tip through veins. The helix is aligned with the radial axis of the electrode and travels through the guiding mechanism. The mesh may be tightly woven or constructed so that there are effectively no openings, or the mesh can be controlled to provide controlled porosity, or controlled flow through the mesh.

In another embodiment, the electrode tip includes a mesh screen forming a protuberance on the end surface of the electrode tip. The protuberance is axially aligned with the radial axis of the electrode. The helix travels around the protuberance as it passes through the mesh while traveling to attach to tissue within the heart. The helix also travels around the protuberance as it is retracted away from the tissue within the heart. If the mesh screen is insulated around the protuberance, then a high impedance tip is created. Advantageously, the protuberance allows for better attachment to the cardiac tissue without having the electrode tip penetrating therethrough.

Additionally, a distal tip electrode is provided including an electrode tip, a mesh screen disposed at a distal end of the electrode tip, a fixation helix disposed within the electrode tip, and a helix guiding mechanism. The electrode tip further may include a piston for moving the helix. The piston further may include a slot for receiving a bladed or fixation stylet. When engaged and rotated, the piston provides movement to the helix. The base provides a mechanical stop for the helix and piston when retracted back into the electrode tip.

In another embodiment, the distal tip assembly is adapted for implantation proximate to the heart while connected with a system for monitoring or stimulating cardiac activity. A fixation helix/piston assembly is housed by an electrode collar, housing, and base assembly. Attached to the proximal end of the helix is a piston which includes a proximal slot for receiving a bladed or fixation stylet. When a stylet is engaged in the slot and rotated, the piston provides movement to the helix. Depending on the embodiment, the fixation helix/piston assembly may be electrically active or inactive. The electrode collar, housing, and base all house the fixation helix/piston assembly. The proximal end of the electrode collar is attached to the distal end of the housing. Furthermore, the proximal end of the housing is attached to the distal end of the base, and the proximal end of the base is directly attached to the conductor coils of the lead.

A mesh screen may be attached to the distal tip of the electrode collar. The mesh screen, in another embodiment, is electrically active and serves as the electrode on the distal tip assembly. The tip may then be fully insulated to increase the impedance of the tip or may be partially insulated (with preselected areas of the helix tip being insulated and other areas being non-insulated) to adjust the impedance of the tip to the specific or optimal levels desired. The area of the mesh screen can be modified to cover differing portions of the end surface of the distal tip assembly to control electrical properties of the lead. The fixation helix travels through a guiding mechanism, where the guiding mechanism allows the fixation helix to be extended and retracted. In one embodiment, the helix guiding mechanism includes a hole formed within the mesh screen. Alternatively, the helix guiding mechanism can include a guiding bar disposed transverse to a radial axis of the electrode collar. The mesh screen and/or guiding bar also serve as a full extension stop when the helix is fully extended. The base serves as a stop when the fixation helix/piston assembly is fully retracted.

The provided electrode tip supplies a retractable helix and a mesh screen which advantageously allows for sufficient tissue in-growth. The guide mechanism provides a convenient way to direct the rotation of the helix. A further advantage of the electrode tip is the provided mechanical stop. The mechanical stop aids in preventing over-retraction of the helix during the installation or removal of the electrode tip.

In yet another embodiment, the electrode uses a partially insulated fixation helix to provide a relatively high pacing impedance electrode. The fixation helix is insulated using insulating coatings over a portion of the fixation helix.

DETAILED DESCRIPTION OF THE INVENTION

In the following detailed description, reference is made to the accompanying drawings which form a part hereof, and in which is shown by way of illustration specific embodiments in which specific aspects of the broader invention may be practiced. These embodiments are described in sufficient detail to enable those skilled in the art to practice both the broad concepts of the invention as well as more limiting specific constructions, and it is to be understood that other embodiments may be utilized and that structural changes may be made without departing from the spirit and scope of the present invention as disclosed herein. Therefore, the following detailed description is not to be taken in a limiting sense, and the scope of the present invention is defined by the appended claims.

As noted previously, there are a number of ways in which increased impedance may be effected for mechanically fastened electrode connections in atrial/ventricular implantable catheters (AVIC) systems. These include at least the following: 1) a fully insulated tissue engaging tip (at least with respect to all surfaces that are in electrical contact or electrically active physical relationship to heart muscles so that a pace would be effective if discharged at that portion of the tip), 2) a partially insulated engaging tip (only a portion of the surface area of the engaging tip being insulated, preferably there is sufficient coating so that there is at least 5%, or at least 10%, or at least 20 or 30%, or at least 40, 50 or 60%, or at least 70, 75, 80 or 90% of the surface area of the tip which can discharge to heart muscle [or as percentages of the entire tip or as percentages of the entire tip that extends physically beyond the end plane of the catheter and which may therefore penetrate tissue or muscle]), 3) a porous, electrically conductive element, such as a mesh or screen of material at the proximal end of the helix or the distal end of the lead (excluding the helix), at the base of an extended engaging tip, 4) the selection of materials in the composition of the mesh and/or tip which provide higher impedance, 5) the partial insulative coating of a porous conductive element, such as the mesh or screen to increase its impedance, and 6) combinations of any of these features. There may be various constructions to effect the increased or high impedance, including the use of helical tips with smaller surface areas (e.g., somewhat shorter or thinner tips). There may also be other elements associated with the catheter and/or leads, such as a sheath of material inert to body materials and fluids, circuitry, microcatheters, and at least one conductor extending through the lead body.

One aspect of the present invention comprises an implantable electrode with a helical tip comprising:

an electrode having a distal end and a proximal end; and a helix disposed within the electrode, which helix is aligned along a radial axis of the electrode towards the distal end, and which helix is either retractable or fixed; and the implantable electrode having at least one feature selected from the group consisting of.

a) the helix having a coating of an insulating material on its surface which covers at least 5% of its surface area but less than 95% of its surface area (which is exposed beyond the distal end of the electrode), b) the helix extending beyond the distal end of the electrode and the distal end of the electrode having a porous conductive surface at a base of the helix, c) a porous conductive element such as a screen or mesh at a base of the helix, which is retractable/extendable, with the helix being either active or inactive (electrically), and d) a partially insulated (partially insulation coated) porous conductive element (e.g., screen or mesh) at the base of an active or inactive, retractable/extendable or fixed helix.

The implantable electrode preferably has the helix with a coating of insulating material on its surface which covers from 5–100% (to 100% where there is an additional electrode element within the system) or 5–95% of surface area of the helix beyond the distal end of the electrode. Alternatively, the surface of the helix is that which is considered to be in electrically discharge-functional physical relationship with tissue or muscle into which it is embedded. For purposes of measuring or determining the distal end of the electrode, the tip extends beyond a tubular or cylindrical housing or structural portion which is considered the electrode, and the tip is an engaging portion that extends beyond the housing portion of the electrode. The distal end of the electrode is usually characterized as the end of the cylindrical housing or tubing carrying the tip, circuits, conductive elements, guides, etc. It is more preferred that the helix of the implantable electrode has a coating of insulating material on it surface which covers from 5–95% or 10–90% of the surface area of said helix beyond the distal end of the electrode.

Figure 1:
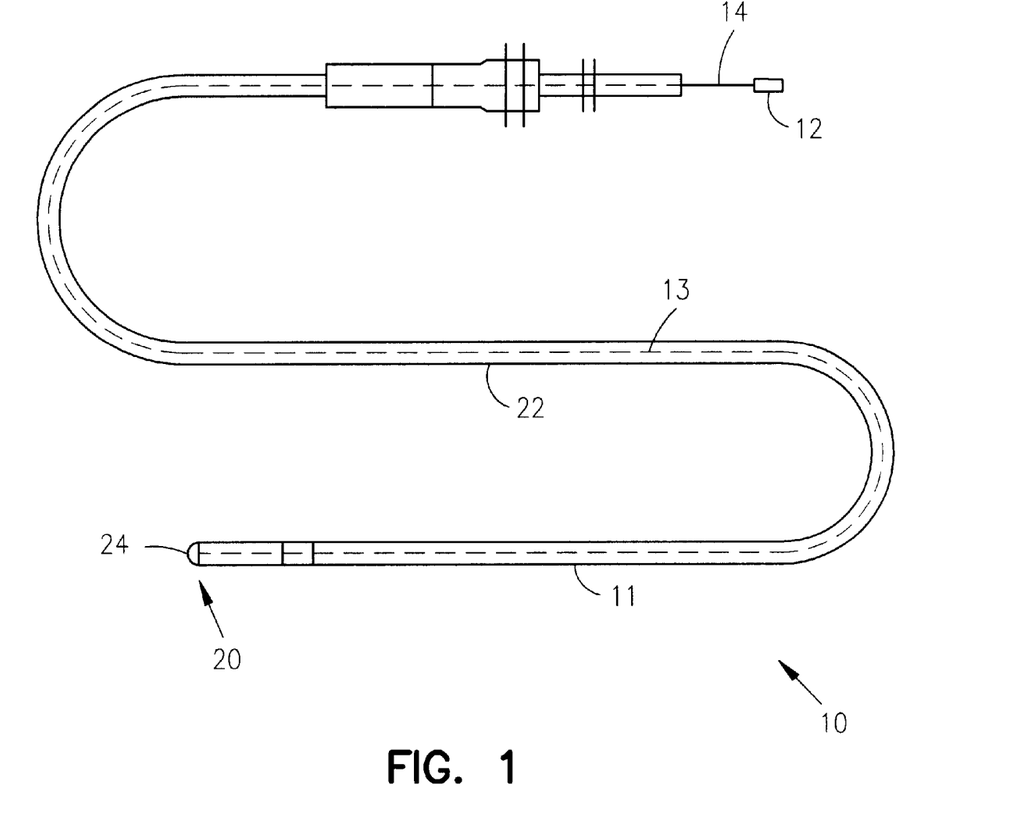
FIG. 1 is a first side elevational view illustrating a lead constructed in accordance with one embodiment of the present invention.

A lead 10 is illustrated in FIG. 1. The lead 10 comprises a lead body 11, an elongate conductor 13 contained within the lead body, and a lead tip 20 with an optional retractable tip assembly 24 contained in the lead tip 20. In addition, a stylet 14 is shown inserted into the lead body 11. A helix 100 (FIGS. 2A–5A), which consists of an electrical conductor coil, is contained in the retractable lead tip 24. In an alternative practice of the invention, the helix 100 extends and retracts by rotation of the stylet 14, as will be discussed further below. A Brady lead body is shown, although the invention could be incorporated with other leads, such as Tachy leads. The lead body 11 consists of electrical conductors 13 which are covered by a biocompatible insulating material 22. Polymers, such as silicone rubber, fluorinated resins, polyacrylates, polyamides ceramic or composite materials or other insulating material can be used for covering the lead body 11.

Figure 3A:
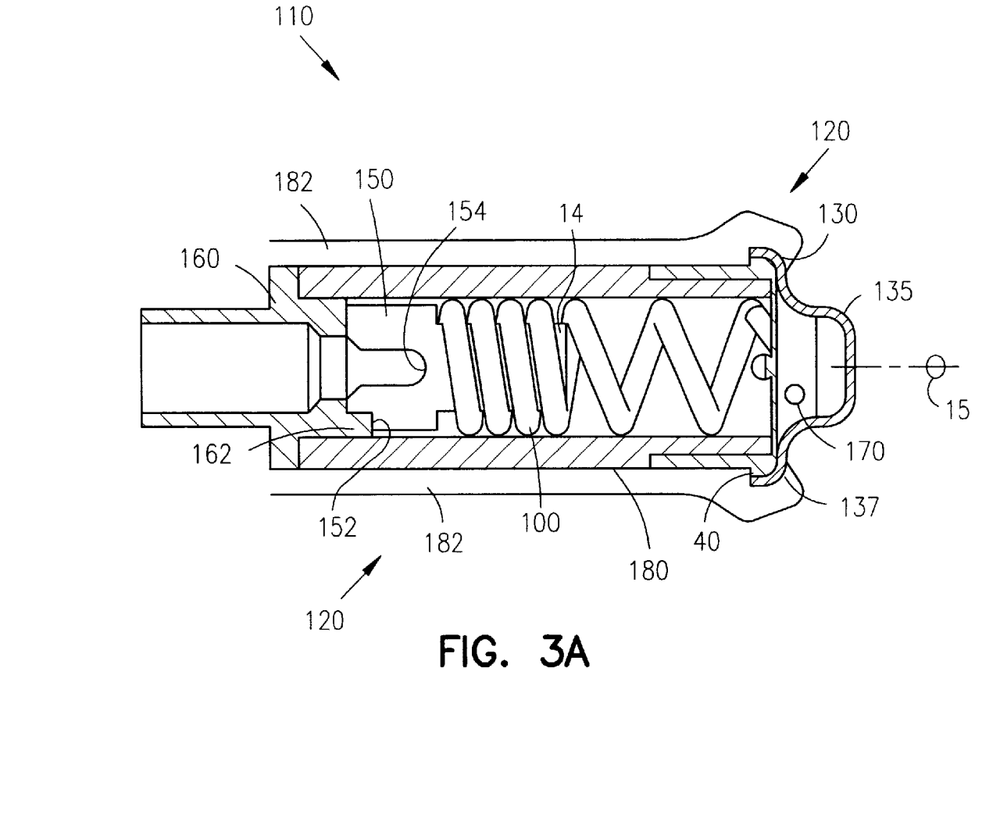
FIG. 3A is a cross-sectional view of an electrode tip of a lead for monitoring and stimulating the heart constructed in accordance with one embodiment of the present invention.

In one embodiment shown in FIG. 3 and 3A, the helix 100 is formed of electrically conductive material offering low electrical resistance and also resistant to corrosion by body fluids. A biocompatible metal, such as titanium or platinum-iridium alloy is an example of a suitable material. Alternatively, the helix 100 is electrically inactive or insulated. In one embodiment, the helix 100 may be coated with an insulative material (not shown) or may be constructed of a rigid, corrosion resistant, non-electrically-conductive material (e.g., a ceramic). A housing 182, described in further detail below, is made from an electrically conductive material and covered with an insulating material such as a synthetic or natural polymer such as a silicone rubber. The housing 182 is directly connected to an electrical conductor within the lead 120. These materials are additionally suitable because they tend to be biologically inert and well tolerated by body tissue.

The helix 100 defines a lumen and thereby is adapted to receive a stiffening stylet 14 that extends through the length of the lead. The stylet 14 stiffens the lead 120, and can be manipulated to introduce an appropriate curvature to the lead, facilitating the insertion of the lead into and through a vein and through an intracardiac valve to advance the distal end of the lead 120 into the right ventricle of the heart (not shown). A stylet knob 154 is coupled with the stylet 14 for rotating the stylet 14 and advancing the helix 100 into tissue of the heart.

Figure 2A:
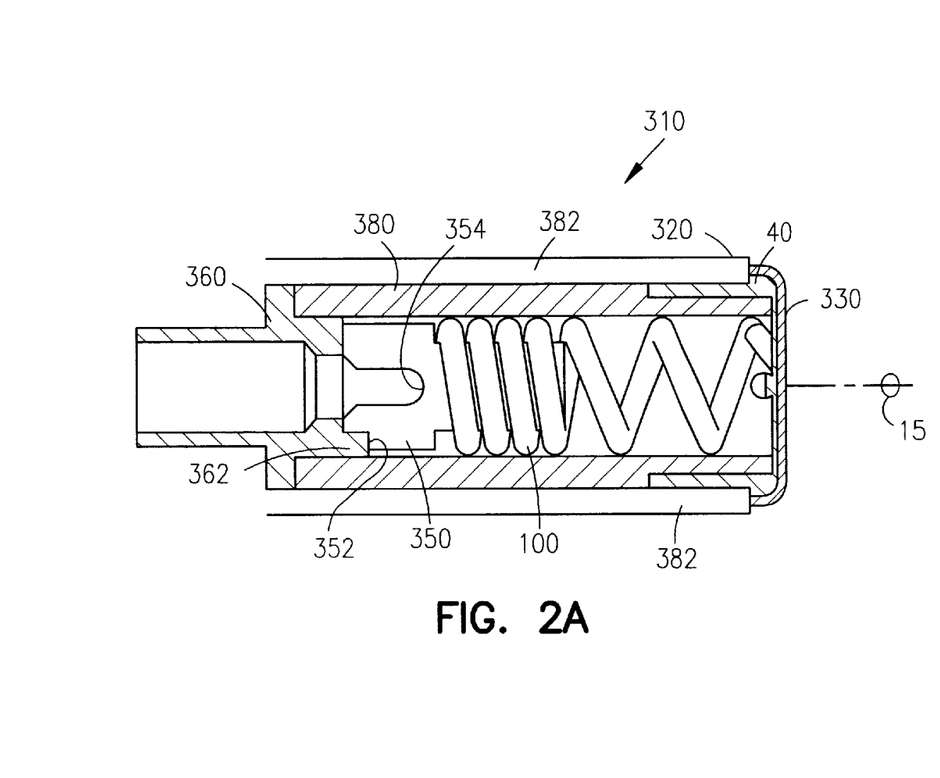
FIG. 2A is a cross-sectional view of an electrode tip of a lead for monitoring and stimulating the heart constructed in accordance with one embodiment of the present invention.
Figure 2B:
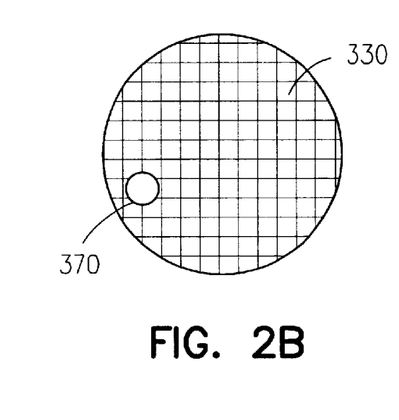
FIG. 2B is an end view of the electrode tip of the lead shown in FIG. 2A.

In one embodiment, as shown in FIGS. 2A and 2B, a lead 310 has an electrode tip 320 which is provided with a mesh screen 330. The mesh screen 330 completely encapsulates the diameter of the lead, and may serve, at least in part, as a pacing/sensing interface with cardiac tissue. If the helix 100 is electrically active, it too can help serve as a portion of a pacing or sensing interface. The mesh screen 330 is of a porous construction, preferably made of electrically conductive, corrosion resistant material. Using a mesh screen 330 having a porous construction allows for fibrotic ingrowth. This provides for a further anchoring of the lead tip 320 and also increases the sensing capability of the lead 310 by increasing the surface area in contact with the cardial tissue. The mesh screen 330 may be attached to an electrode collar 40, which is electrically active. In a retractable catheter system, a housing 380, which is electrically conductive, encapsulates the piston 350 and the fixation helix 100. Insulation 382 is disposed about the housing 380 and collar 40.

Disposed within the lead 310 is a lead fastener 100 for securing the lead 310 to cardiac tissue. The lead fastener 100 can be disposed along the radial axis 15 of the electrode lead 310. In this embodiment, the lead fastener comprises a fixation helix 100. The fixation helix 100 can be made electrically active or inactive as discussed above. Attached to the fixation helix 100 in a retractable tip system is a piston 350. The piston 350 is configured to mate with a bladed locking stylet 14 at a stylet slot 354, and acts as an interface between the stylet 14 and the helix 100. The stylet 14, coupled with the piston 350 at the stylet slot 354, extends and retracts the fixation helix 100 when the stylet 14 is rotated. The piston 350 can either be electrically active or inactive. The piston 350 also has a slot 352, which allows the piston 350 to mate with a base 360.

Fitted with a knob 362, as shown in FIG. 2A, the base 360 mates with the slot 352 of the piston 350. The base 360 serves as a stop once the fixation helix 100 is fully retracted. The electrically conductive base 360 also allows passage of a bladed locking stylet 14 and attachment of electrode coils (not shown).

In addition, the lead 310 has a guide groove 370. The groove 370 is formed by puncturing a hole (not shown) within the mesh screen 330, although the guide groove 370 can be formed by other methods known by those skilled in the art. Having a circular cross-section, the guide groove 370 may have a diameter greater than that of the conductor forming the helix 100. The groove 370 is disposed within the mesh screen 330, and directs the fixation helix 100 from its retracted position, as illustrated in FIG. 2A, to an extended position (not shown). The groove 370 also reversibly directs the fixation helix 100 from an extended position to the retraction position.

Figure 3B:
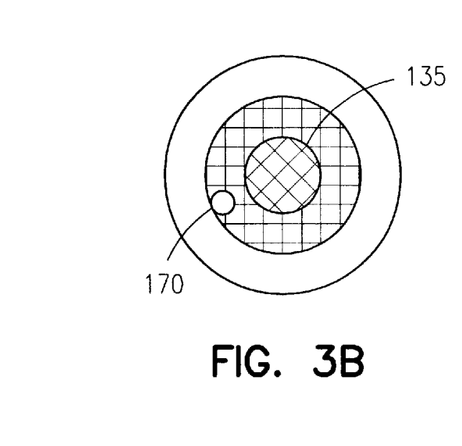
FIG. 3B is an end view of the electrode tip of the lead shown in FIG. 3A.

In a second embodiment, as shown in FIGS. 3A and 3B, a lead 110 has an electrode tip 120 which is provided with a mesh screen 130. The mesh screen 130 completely encapsulates the diameter of the lead or electrode tip 120, and serves as the pacing/sensing interface with cardiac tissue. The screen 130 is of a porous construction, made of electrically conductive, corrosion resistant material. Using a mesh screen 130 having a porous construction allows for fibrotic ingrowth. This provides for a further anchoring of the lead tip 120 to tissue and also increases the sensing capability of the lead 110. The sensing capability is enhanced because the mesh screen 130 has more surface area than corresponding solid material. The ingrowth of fibrotic tissue into the mesh screen 130 increase the sensing capability of the lead 110 by increasing the surface area in contact with the cardiac tissue. Furthermore, the geometry of the mesh screen 130, particularly any protuberance, as will be discussed below, creates a high pacing impedance tip.

The mesh screen 130 may form a protuberance 135 from a flat edge portion 137 of the mesh screen 130 in a generally central portion of the electrode tip 120. The protuberance 135 may be generally circular in cross-section, but may be any shape (e.g., truncated cylindrical, truncated pyramidal, oval, ellipsoidal, etc.) as a result of design or circumstance which provides a flat or conformable surface (preferably not a rigid, sharp face which will not conform to tissue) abutting tissue, and preferably has a diameter smaller than a diameter of the lead 110. In addition, the protuberance 135 is aligned with the radial axis 15 of the lead 110. Sintered to an electrode collar 40, a process known by those skilled in the art, the mesh screen 130 is attached to the electrode tip 120. The electrode collar 40 is electrically active.

Disposed within the electrode lead 110 is a lead fastener for securing the electrode lead 110 to cardiac tissue. The lead fastener can be disposed along the radial axis 15 of the electrode lead 110. In this embodiment, the lead fastener comprises a fixation helix 100. The fixation helix 100 can be made electrically active or inactive to change sensing and pacing characteristics, as discussed above. Attached to the fixation helix 100 is a piston 150. The piston 150 is configured to mate with a bladed locking stylet 14, thereby providing a movement assembly. The stylet 14 extends and retracts the fixation helix 100 when the stylet 14 is rotated. The piston 150 can either be electrically active or inactive. The piston 150 also has a slot 152. The slot 152 of the piston 150 allows the piston 150 to mate with a base 160 upon full retraction.

The base 160 is modified with a knob 162 to mate with the slot 152 of the piston 150. The knob 162 mates with the piston 150 to prevent over-retraction once the helix 100 has been fully retracted. The stylet 14 operates to advance the fixation helix 100. As the implanter rotates the stylet 14, the stylet 14 engages the piston 150 at the stylet slot 154 and rotates the piston 150, which moves the fixation helix 100 through a guide groove 170. The guide groove 170 is for ensuring that the fixation helix 100 is properly guided out of and into the end of the electrode. Once the fixation helix 100 is fully retracted, the base 160 serves as a mechanical stop. The base 160 also allows passage of a bladed locking stylet 14 and attachment of electrode coils. Additionally, the base 60 is electrically active.

The electrode lead 110 also has a guide groove 170. The groove 170 is formed by puncturing a hole within the mesh screen. Having a circular cross-section, the groove 170 has a diameter greater than that of the conductor forming the helix 100. The groove 170 is disposed within the mesh screen 130, and directs the fixation helix 100 from its retracted position, as illustrated in FIG. 2A, to an extended position (not shown). During implantation, after the electrode is in contact with tissue at the desired location in the heart, the stylet 14 is rotated which causes the piston to advance the fixation helix out of the groove 170. As the fixation helix 100 is placed in an extended position, the helix 100 travels through groove 170 and circles around the protuberance 135. The groove 170 also directs the fixation helix 100 from an extended position to the retracted position. Advantageously, the mesh screen 130 prevents the implanter from overextension and advancing the helix 100 too far into the tissue. An electrically conductive housing 180 encapsulates both the piston 50 and the fixation helix 100. Insulation 182 covers the housing 180, the collar 40, and a portion of the mesh screen 130. The insulation 182 over the mesh screen 130 controls the impedance of the electrode tip 120.

Figure 4A:
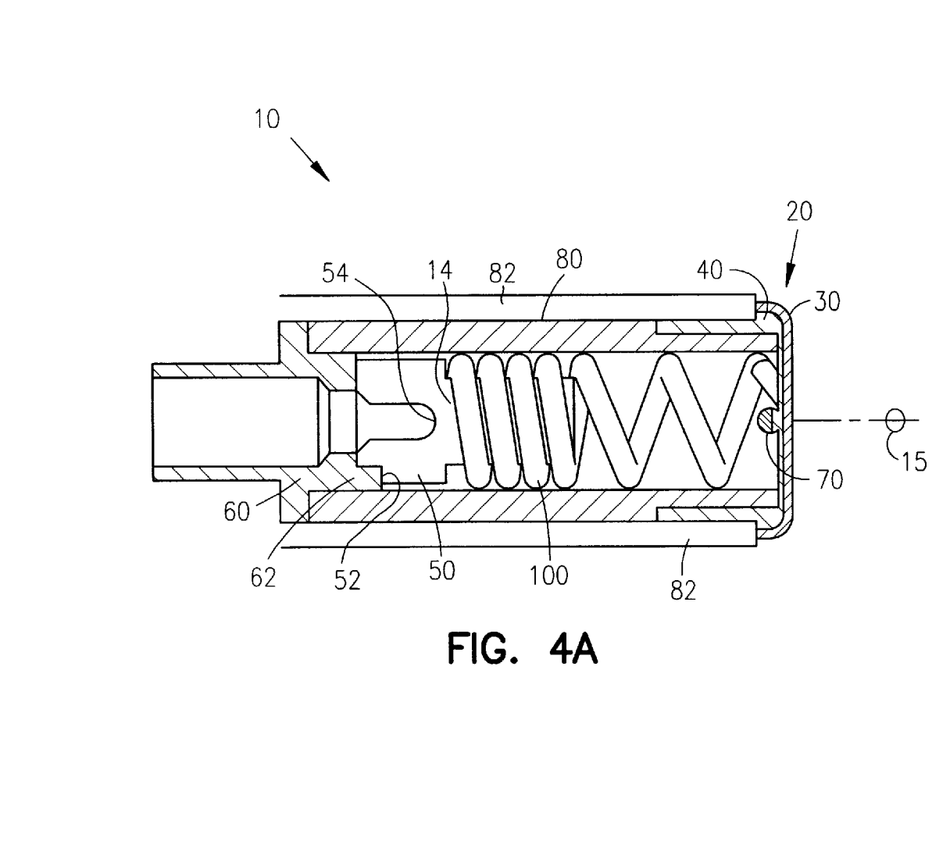
FIG. 4A is a cross-sectional view of an electrode tip of a lead for monitoring and stimulating the heart constructed in accordance with one embodiment of the present invention
Figure 4B:
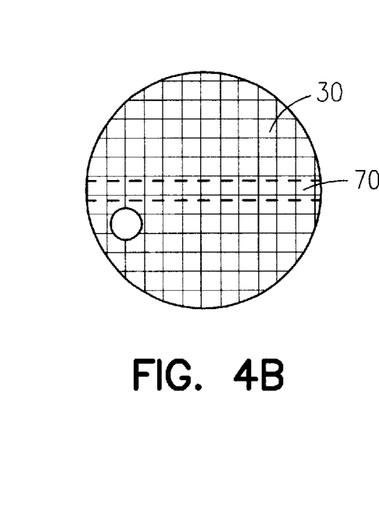
FIG. 4B is an end view of the electrode tip of the lead shown in FIG. 4A.

In a third embodiment as shown in FIGS. 4A and 4B, a lead 10 has an electrode tip 20 which is provided with a mesh screen 30. The mesh screen 30 completely encapsulates the diameter of the lead tip. Sintered to an electrode collar 40, the mesh screen 30 is attached to the electrode tip 20. The electrode collar 40 is electrically active. A housing 80 is disposed about the helix 100, and is electrically active. Insulation 82, encompasses the housing 80 and collar 40.

Disposed within the lead 10 is a lead fastener for securing the lead 10 to cardiac tissue. The lead fastener can be disposed along the radial axis 15 of the lead 10. In this embodiment, the lead fastener comprises a fixation helix 100. The fixation helix 100 can be made electrically active or inactive to change sensing and pacing characteristics.

The helix 100 is of a well known construction. Using a conductor coil such as helix 100 has been shown to be capable of withstanding constant, rapidly repeated flexing over a period of time which can be measured in years. The helix 100 is wound relatively tightly, with a slight space between adjacent turns. This closely coiled construction provides a maximum number of conductor turns per unit length, thereby providing optimum strain distribution. The spirally coiled spring construction of helix 100 also permits a substantial degree of elongation, within the elastic limits of the material, as well as distribution along the conductor of flexing stresses which otherwise might be concentrated at a particular point.

Attached to the fixation helix 100 is a piston 50. The piston 50 is configured to mate with a bladed locking stylet 14. The piston 50 advances the fixation helix 100 once the lead is placed in position within the heart. The piston 50 can either be electrically active or inactive. The piston 50 also has a slot 52 and a stylet slot 54. The stylet 14 couples with the stylet slot 54 and extends or retracts the fixation helix 100 when the stylet 14 is rotated. The slot 52 of the piston 50 allows the piston 50 to mate with a base 60 when the helix 100 is retracted to prevent over retraction. The base 60 is configured with a knob 62 to mate with the slot 52 of the piston 50. Once the fixation helix 100 is fully retracted, the base 60 serves as a stop at full retraction. The base 60 also allows passage of a bladed locking stylet 14 and attachment of electrode coils. In addition, the base 60 is electrically active.

The lead 10 also includes a guiding bar 70. Extending across the diameter of the tip, the guiding bar 70 is generally cylindrical in shape. The guiding bar 70 directs the fixation helix 100 from its retracted position, as illustrated in FIG. 2A, to an extended position (not shown) as the piston 52 advances the helix 100. The guiding bar 70 also directs the fixation helix 100 as it is retracted from an extended position to the retraction position through the mesh screen. Although a guiding bar 70 is described, other types of guiding mechanisms can be used such as helical passageways, threaded housings, springs, and are considered within the scope of the invention. Additionally, the lead 10 is provided with a seal (not shown) for preventing entry of body fluids and tissue from entering the lead through the opening therein. The seal could be a puncture seal between the piston 50 and the base 60. Alternatively, O-rings could be used to seal the electrode.

Figure 5A:
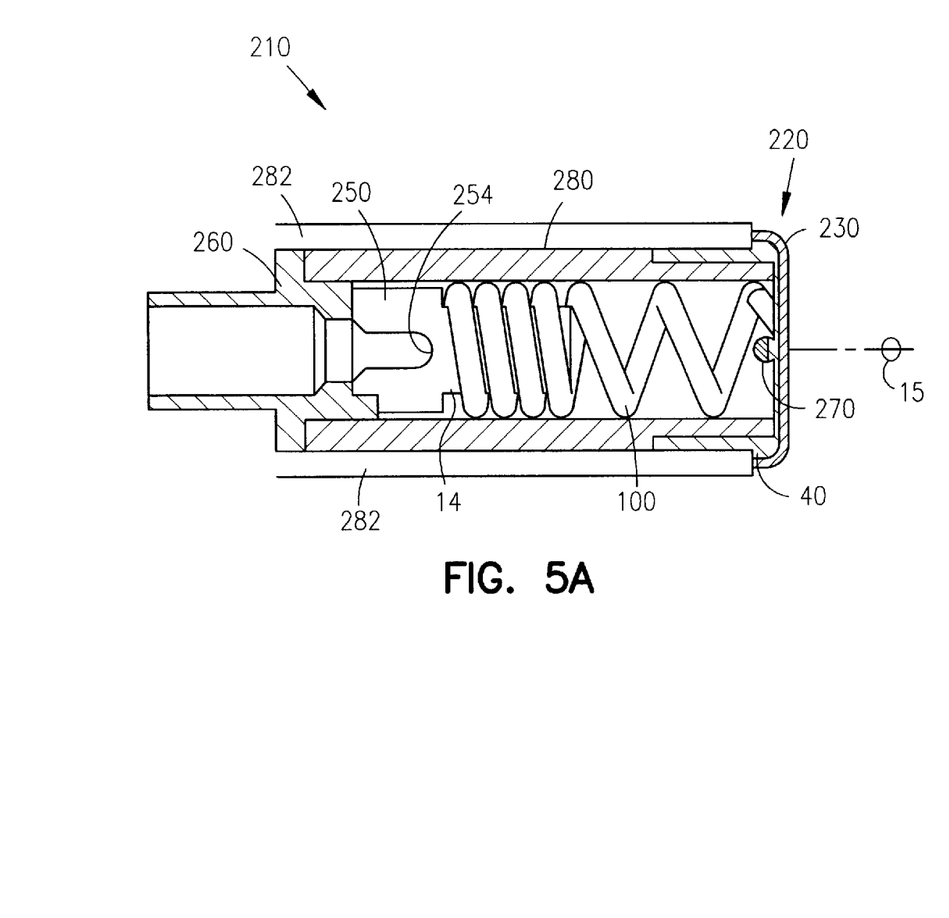
FIG. 5A is a cross-sectional view of an electrode tip of a lead for monitoring and stimulating the heart constructed in accordance with one embodiment of the present invention
Figure 5B:
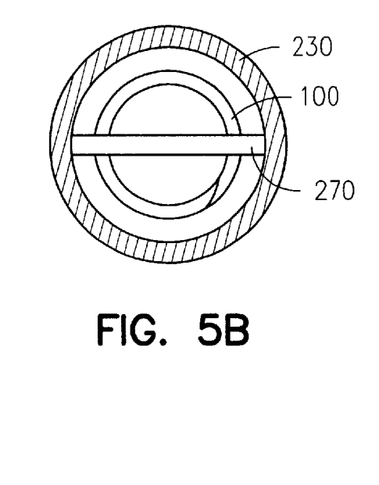
FIG. 5B is an end view of the electrode tip of the lead shown in FIG. 5A.

In a fourth embodiment as shown in FIGS. 5A and 5B, a lead 210 has an electrode tip 220 which is provided with a mesh screen 230. The mesh screen 230 forms an annular ring having an open center, where the annular ring is centered at a radial axis 15 of the electrode lead 210. The mesh screen 230 provides more surface area than a smooth tipped electrode which aids in sensing. The removal of the center portion of the mesh screen creates a high impedance pacing tip due to the nature of the surface geometry. Sintered, fused, bonded, adhesively secured or mechanically attached to an electrode collar 40, the mesh screen 230 is attached to the electrode tip 220. The electrode collar 40 is electrically active.

Disposed within the lead 210 is a lead fastener for securing the lead 210 to cardiac tissue. The lead fastener can be disposed along the radial axis 15 of the electrode lead 210. In this embodiment, the lead fastener comprises a fixation helix 100. The fixation helix 100 can be made electrically active or inactive as discussed above. Attached to the fixation helix 100 is a piston 250. The piston 250 has a stylet slot 254 and is configured to mate with a bladed locking stylet 14. The stylet 14, coupled with the piston 250 at the stylet slot 254, extends and retracts the fixation helix 100 when the stylet 14 is rotated. The piston 250 can either be electrically active or inactive. The base 260 serves as a stop once the fixation helix 100 is fully retracted. The base 260 also allows passage of a bladed locking stylet 14 and attachment of electrode coils. The base 60 is electrically active.

Additionally, the electrode lead also has a guiding bar 270. The guiding bar 270 directs the fixation helix 100 from its retracted position, as illustrated in FIGS. 5A and 5B, to an extended position (not shown). The guiding bar 270 also directs the fixation helix 100 from an extended position to the retracted position. Although guiding bar 270 has been described, other types of mechanisms could be used to extend the helix, and are considered within the scope of the invention. A housing 280 encapsulates the piston 250 and the fixation helix 100, and insulation 282 is disposed over the housing 280 and collar 40.

Insulation generally covers the housing, the collar, and a portion of the electrical discharge surface (e.g., the cathode, the helix and/or the porous material or mesh). The insulation over the mesh screen further controls the impedance of the electrode tip. The insulated coating, whether present on the helix or the mesh or other elements which are potentially electrically active or on which electrical activity is to be suppressed, should be biocompatible, non-thrombogenic, and otherwise safe for implantation. The insulation coating should be of dimensions which effect the insulation, increase the impedance (where desired), but which dimensions do not interfere with the performance of the tip, the lead or the helix or the health of the patient. The insulation is present as a coating ( a material which tends to conform to the surface rather than completely reconfigure it, as would a lump of material). The coating usually should be at least 0.5 microns in thickness, usually between 0.5 and 100 microns, preferably between 1.0 and 30 or 50 microns, more preferably between 1 and 20 microns, still more preferably between 1.5 and 15 microns, and most preferably between 1.5 or 2.0 microns and 10 or 15 microns. The coating may be provided by any convenient process, such as electrophoretic deposition, dip coating, spin coating, in situ polymerization, vapor deposition, sputtering and the like. Any insulating material is useful, such as polymers, ceramics, glasses, and the like, but because of their convenience in application, flexibility and availability, polymers are preferred. Polymers from such classes as polyesters, polyamides, polyurethanes, polyethers, polysiloxanes, polyfluorinated resins, polyolefins, polyvinyl polymers, polyacrylates (including polymethacrylates), and the like may be used with various leads and tips according to the practice of the present invention. PARYLENE is a preferred material, as described herein, with a thickness of between 1.5 and 10 microns.

In yet another embodiment, a partially insulated fixation helix is used to provide a relatively high impedance electrode design. Leads comprising a distal or electrode end and a proximal or connector end may be used. A "miniature" wire-in-basket porous electrode may be sintered upon the distal end of a metallic pin, provided with a blind hole. Circumferential to this subassembly, a sharpened wire fixation helix may be positioned and attached at a general location proximal to the electrode by any convenient means which allows electrical continuity. This attachment includes, but is not limited to, crimping, spot welding, laser welding, the use of grooves upon the surface of the pin, the use of thin metallic overband (also not shown) or any combination thereof. A portion of this fixation helix is provided with an extremely thin layer of a biostable, biocompatible polymer, which, inter alia, provides electrical insulation between the fixation helix and the cardiac tissue. In one embodiment, the insulated portion is the majority of the fixation helix, leaving a relatively small uninsulated region of fixation helix. This approach offers increased impedance to reduce energy dissipation in pulsing functions, such as pacing functions. Other varying embodiments include, but are not limited to, a portion which is approximately or substantially equal to half of the fixation helix, and a portion which is approximately or substantially equal to a minority of the fixation helix. Such embodiments provide different amounts of uninsulated region and different amounts of impedance. The thin coating of electrically insulating coating must usually be at least 1 micron in thickness to provide a significant insulating effect, depending upon its insulating ability and properties. The thickness of the coating is limited primarily by physical limitations on the system. The coating can not be so thick as to interfere with the fastening ability of the helix or to increase the size of the helix beyond that which is tolerable for the use of the helix and the patient. Typically, the coating is at least one micron up to about 100 microns, more typically the coating is between 1 and 30 microns, preferably between 1.5 and 20 microns, more preferably between 1.5 and 15 microns, and most preferably between 2 and 10 microns. The material used for the coating should, of course, be biocompatible and even more preferably non-thrombogenic. Materials such as PARYLENE™, polyurethanes, polyacrylates (including polymethacrylates), polyesters, polyamides, polyethers, polysiloxanes, polyepoxide resins and the like can be used. Crosslinked polymers within these classes may be preferred for their resistance to breakdown and their physical durability. As the coating is to be maintained within the body of a recipient, the coating composition should not be water-soluble or aqueous soluble within the parameters and environment encountered within animal bodies (e.g., it should not be soluble within blood, serum or other body fluids with which it might come into contact).

To the proximal end of this pin, a metallic conductor coil may be conveniently attached to provide electrical connection to the implantable pacemaker (not shown) by means of a connector. In one embodiment, local (e.g., steroid or other medicinal) therapy is provided by a (e.g., circumferential) steroid/polymer matrix positioned immediately proximal to the porous electrode. In one embodiment, the circumferential steroid/polymer matrix is provided with a distal taper. Other embodiments include other distal configurations, including, but not limited to, non-tapered or "inflated" configurations. In one embodiment, an internalized, medicinal or biologically active (e.g., steroid) releasing matrix is used. Proximal to this biologically active (e.g., steroid) eluting matrix, a generally cylindrical polymeric tubing (this is the preferred shape, but the shape is a matter of choice) 820 is used to provide electrical insulation of this entire assembly. In one embodiment, the lead is "unipolar." In one embodiment, an ablative protective covering positioned over the entirety of distal end is used (not shown). One example of such a covering is the mannitol "Sweet Tip"® electrode of Guidant Corporations's Cardiac Rhythm Management Group. In one embodiment, a "bipolar" lead is provided with the distal electrode features described.

During an in vitro evaluation of this electrode design, polymeric coatings intended to partially insulate the fixation helix were prepared and evaluated. In one embodiment, the PARYLENE coating is extremely thin (~3µ), providing a coating with uniform coverage which is adherent to the metallic substrate, and which is controllable to provide an abrupt margin. The silicone rubber coating is known to be somewhat thicker (~10µ), uniform in coverage, somewhat less adherent to the metallic substrate, and controllable to an abrupt margin. Other coatings may be used without departing from the spirit and scope of the present invention.

The PARYLENE or other insulative coating effectively increases in vitro "pacing impedance." Application of a non-continuous or partially extensive coating of an electrically insulating polymer such as PARYLENE to the metallic fixation helix produces the desired increase in impedance compared to an uninsulated helix as well as other existing designs. For example, it has been demonstrated that one embodiment using a coated fixation helix provides a pacing impedance of over approximately 800 ohms which is larger than the impedance of some electrodes using an uncoated fixation helix. The post-implant pacing impedance of an embodiment using a coated fixation helix remains higher than that of typical electrodes using an uncoated fixation helix. In one experiment, a coated fixation helix using PARYLENE as an insulating layer provided over 1200 ohms average pacing impedance on the day of implantation and over 900 ohms ten days after the implant.

Additionally, post-implant average voltage threshold of the PARYLENE insulated miniaturized electrode is less than the other high impedance electrodes. Such performance is considered to be desirable. In one experiment, an embodiment with a coated fixation helix 802 having a voltage threshold of approximately 0.2 volts on the day of implant was measured at about 0.7 volts at ten days after the implant (using a 0.5 ms pulse width). An electrode with an uncoated fixation helix demonstrated over 0.8 volts average voltage threshold at ten days after the implant, illustrating the benefits of the coated fixation helix.

An additional benefit is that the coated fixation helix embodiments may provide an improvement in both the implant as well as post-implant average S-wave amplitude detection.

The miniaturized high impedance, positive fixation porous electrode technology described here provides the following advantages over the prior art. For one example, the coated fixation helix embodiments provide an electrode where the benefits of high impedance pacing are realized through downsizing the porous electrode and insulating the fixation helix. Downsizing of the porous electrode may be accomplished, for example, by having a smaller porous (e.g., mesh) electrode supported on a non-conductive surrounding support element (e.g., a polymeric or composite film with a mesh central area, particularly a mesh truncated conical or pyramidal area of flexible, conductive mesh). An area of the completely conductive mesh may also be discontinuously coated leaving a conductive central or conductive raised area, particularly surrounding a contact, engaging element, or helix. Further, an external steroid collar provides a fabrication advantage since such a component can be readily mass produced compared to smaller components with elaborate profiles. Still further, fabrication of a lead with this external collar is streamlined. The higher impedance design conserves battery power to provide longer battery life with fewer battery replacements. Other benefits exist which are not described in detail herein, however, which those skilled in the art will appreciate.

Figure 6:
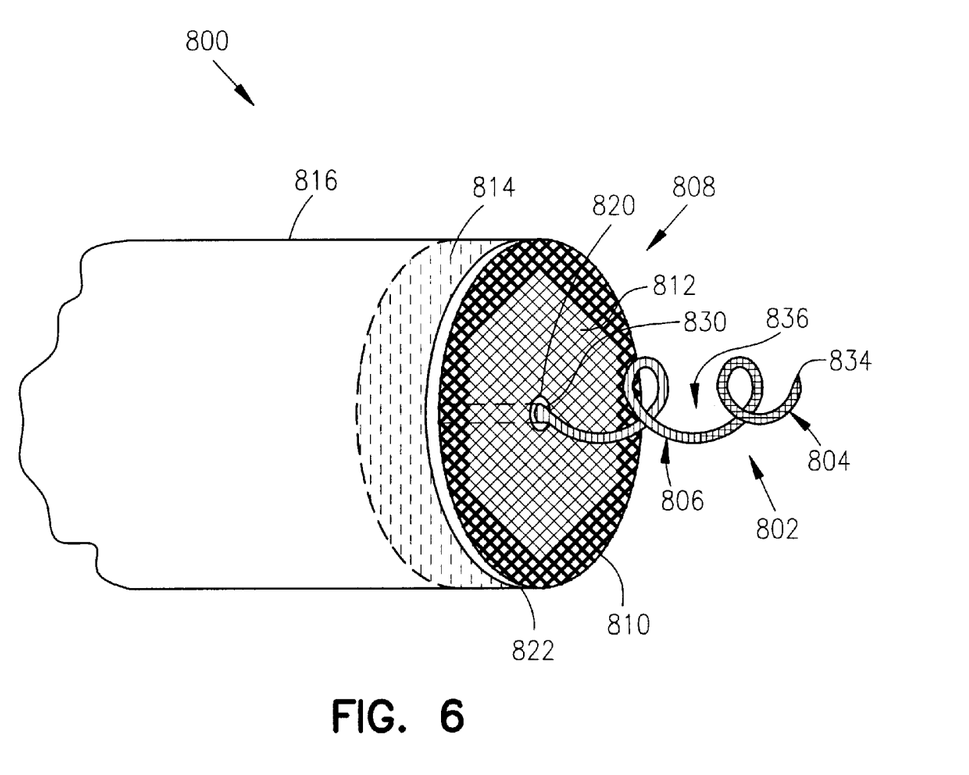
FIG. 6 shows a partially insulated helical tip according to the present invention which increases the impedance of the tip as compared to a fully non-insulated helical tip.

FIG. 6 shows a high impedance catheter tip 800 with a partially insulated tip 802 and a partially insulated mesh 808. The partially insulated tip (or helix) 802 extends from a base, proximal end 830 to a distal, pointed end 834 with a middle portion 836 lying between proximal end 830 and distal end 834. Helix 802 comprises one fully insulated section 804 which begins at distal, pointed end 834 and extends to, and ends within, middle portion 836 and one uninsulated section 806 which extends from the end of the fully insulated section within middle portion 836 to base, proximal end 830. The partially insulated mesh 808 comprises a first area 810 of the mesh 808 which is insulated and second are 812 of the mesh 808 which is not insulated. The impedance of the catheter tip can be readily controlled by the amount of surface area of the helical tip itself and the area of the mesh (if present) which is insulated. With a fixed conductivity in the tip and the mesh (if present), the impedance can be increased by increasing the percentage of the surface area of the tip or mesh which is insulated.

A hole 820 is shown in the mesh 808. The mesh 808 may be flat and flush with the end 822 of the catheter 816 or may be partially wrapped (not shown) over the end 820 or inside the end 820 to affix the mesh to the catheter 816. The mesh 808 may also be hemispherical, truncated conical, truncated pyramidal or any other shape which may assist in allowing the mesh 808 to more compliantly contact tissue (not shown) surface to transmit the pacing signal or discharge. Within the catheter 816 may be a soluble, elutable or dispersible material which carries medication or biologically active material along with the catheter. For example, anti-inflammatants, antibiotics, analgesics, pain-reducing medication, vitamins, anti-viral medication, or the like may be transmitted to the attachment site along with the catheter by inclusion within a material 814 carried within or on the catheter 816.

The coating of insulation on the helical tip or mesh may be applied by any convenient method, including, but not limited to coating (e.g., dip coating), printing, spraying, brush application, resist application and removal and the like. The insulation may also contain active ingredients (such as those recited within material 814) to benefit the patient. The insulation carrying the active material must not be soluble, so a polymer or other material that is porous or has elutable materials must be used. The material delivery does not have to be coextensive with the life of the implant or the tip, and delivery of the material may be desirable only over a short time period after insertion of the helical tip and catheter.

A soluble or dispersible protective cap may also be placed over the helical tip to reduce the possibility of any incidental damage while catheterizing or moving the tip within a patient. As previously noted, the cap material should preferably be biocompatible or even digestible and may include such materials as natural and synthetic materials such as sugars, starches, gelation (unhardened), gums, resins, polymers, and the like. All components of the catheter and tip which are exposed to the tissue or fluids within a patient should be non-thrombogenic, and bio-acceptable. There are extensive classes of commercially available materials which meet these needs for metal, polymeric, composite and other materials described within the practice of the present invention.

It is to be understood that the above description is intended to be illustrative, and not restrictive. Although the use of the lead has been described for use in a cardiac pacing system, the lead could as well be applied to other types of body stimulating systems. Many other embodiments will be apparent to those of skill in the art upon reviewing the above description. The scope of the invention should, therefore, be determined with reference to the appended claims, along with the full scope of equivalents to which such claims are entitled.

What is claimed:

1. An endocardial lead comprising:
  a lead body having a conductive wire therein;
  an electrode connected to the conductive wire, the electrode having a distal electrode end and a proximal end;
  a helix coupled with said electrode, said helix aligned along a radial axis of the lead body and the electrode at said distal electrode end, the helix having a base, proximal end and a distal, pointed end with a middle helix portion extending between the proximal end of the helix and the distal, pointed end of the helix, wherein at least a portion of the helix has an insulating coating disposed thereon, wherein the insulting coating extends over a section of the helix beginning at the distal, pointed end of the helix and ending in the middle portion of the helix such that there is an insulated section of the helix extending from the middle portion of the base, proximal end of the helix; and a porous conductive surface at the distal electrode end of the electrode having an insulting coating partially covering the surface of said porous conductive surface.

2. The endocardial lead of claim 1, wherein said helix is defined in part by an outer surface, wherein said helix outer surface is disposed beyond said distal electrode end.

3. The endocardial lead of claim 1, wherein the porous conductive surface includes a mesh surface.

4. The endocardial lead of claim 1, wherein said porous conductive surface at said distal electrode end of said electrode comprises a mesh, wherein said mesh comprises an electrically conducting surface.

5. The endocardial lead of claim 4, wherein said mesh is electrically conductive, and said mesh is adapted to be coupled with at least one electronically active component.

6. An endocardial lead comprising:

a lead body having a conductive wire therein;

an electrode connected to the conductive wire, the electrode having a distal electrode end and a proximal end;

a helix coupled with said electrode, said helix aligned along a radial axis of the lead body and the electrode at said distal electrode end, the helix being adapted for screwing into a heart tissue, the helix having a base, proximal end and a distal, pointed end with a middle helix portion extending between the proximal end of the helix and the distal, pointed end of the helix, wherein at least a portion of the helix has an insulating coating disposed thereon, wherein the insulating coating extends over a section of the helix beginning at the distal, pointed end of the helix and ending in the middle portion of the helix such that there is an uninsulated section of the helix extending from the middle portion of the helix to the base, proximal end of the helix; and a mesh surface at the distal electrode end of the electrode.

7. The endocardial lead of claim 6, wherein the distal electrode end is defined by an end surface, and said mesh surface covers the entire end surface.

8. The endocardial lead of claim 6, wherein the mesh surface includes an insulating coating partially covering the mesh surface.

9. An endocardial lead comprising:

a lead body having a conductive wire therein;

an electrode connected to the conductive wire; and a fixation helix coupled with said electrode and adapted for being screwed into a heart tissue, said helix aligned along a radial axis of the lead body when the fixation helix is implanted in the heart tissue, the helix having a base, proximal end and a distal, pointed end with a middle helix portion extending between the proximal end of the helix and the distal, pointed end of the helix, said helix defined in part by an outer surface having a coating of an insulating material extending over a section of the helix beginning at the distal, pointed end of the helix and ending in the middle portion of the helix such that there is an uninsulated section of the helix extending from the middle portion of the helix to the base, proximal end of the helix.

10. The endocardial lead of claim 9, wherein a distal electrode end of said electrode includes a porous conductive surface.

11. The endocardial lead of claim 10, wherein the porous conductive surface has an insulating coating at least partially covering the porous conductive surface.

12. The endocardial lead of claim 9, wherein an outer diameter of the fixation helix is smaller than an outer diameter of the lead body.

13. An endocardial lead, comprising;

a lead body having a conductive wire therein;

a electrode connected to the conductive wire; and a fixation helix located at a distal tip of the lead body and axially with the lead body when the fixation helix is implanted in a heart tissue, the fixation helix having a distal, pointed end for screwing into the heart tissue and having a base, proximal end with a middle helix portion extending between the proximal end of the helix and the distal, pointed end of the helix, said fixation helix having a surface with an electrically insulating coating thereon, said electrically insulating coating extends over a section of the helix beginning at the distal, pointed end of the helix, and ending in the middle portion of the helix such that there is an insulated section of the helix extending from the middle portion of the helix to the base, proximal end of the helix.

14. The endocardial lead of claim 13, wherein the electrical insulating coating comprises a thermoplastic film polymer based upon para-xylylene.

15. The endocardial lead of claim 13, wherein the electrical insulating coating has a thickness of about 0.5–100 microns.

16. The endocardial lead of claim 13, wherein the electrical insulating coating comprises a polymeric coating.

* * * * *

UNITED STATES PATENT AND TRADEMARK OFFICE
CERTIFICATE OF CORRECTION

PATENT NO.    : 6,501,994 B1
DATED         : December 31, 2002
INVENTOR(S)   : Jeffrey T. Bartig et al.

It is certified that error appears in the above-identified patent and that said Letters Patent is hereby corrected as shown below:

<u>Title page,</u>
Item [56], References Cited, U.S. PATENT DOCUMENTS, insert -- 128/419D -- after "Mirowski"; insert -- 128/404 -- after "Friedman"; insert -- 128/419D -- after "Mirowski et al."; insert -- 128/418 -- after "Thalen et al."; delete "607/126" after "Babotai" and insert -- 607/127 -- therefor.
FOREIGN PATENT DOCUMENTS, delete "0 42551" and insert -- 042551 -- therefor.
Item [74], *Attorney, Agent, or Firm*, insert -- , -- after "Kluth".

<u>Column 2,</u>
Line 33, insert -- ) -- after "sorbitol)".

<u>Column 12,</u>
Line 21, insert -- Parylene material includes a thermoplastic film polymer base upon para-xylylene. -- after "used."

<u>Column 15,</u>
Line 6, delete "insulated" and insert -- uninsulated -- therefor.
Line 8, insert -- helix to the -- before "base".
Line 13, insert -- and said -- after "helix".

<u>Column 16,</u>
Line 25, delete ";" after "comprising" and insert -- : -- therefor.
Line 27, insert -- tip -- before "electrode".
Line 29, insert -- aligned -- after"axially".
Line 39, delete "insulated" and insert -- uninsulated -- therefor.

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,501,994 B1  Page 1 of 2
DATED : December 31, 2002
INVENTOR(S) : Janke et al.

It is certified that error appears in the above-identified patent and that said Letters Patent is hereby corrected as shown below:

<u>Title page,</u>
Item [56], References Cited, U.S. PATENT DOCUMENTS, below "4,030,508", insert
--

| | | | |
|---|---|---|---|
| 4,033,355 | 07/1977 | Amundson | 128/404 |
| 4,038,703 | 08/1977 | Bokros | 3/1.5 |
| 4,082,087 | 04/1978 | Howson | 128/2.06 |
| 4,146,037 | 03/1979 | Flynn et al. | 128/419 |
| 4,156,429 | 05/1979 | Amundson | 128/419 |
| 4,187,853 | 02/1980 | Barton et al. | 128/419 |
| 4,235,246 | 11/1980 | Weiss | 128/758 |
| 4,299,239 | 11/1981 | Weiss et al. | 128/785 |
| 4,326,534 | 04/1982 | Axelgaard et al. | 128/421 |
| 4,587,975 | 05/1986 | Salo et al. | 128/693 |
| 4,667,686 | 05/1987 | Peers-Travarton | 128/785 |
| 4,679,572 | 07/1987 | Baker, Jr. | 128/786 |
| 4,693,258 | 09/1987 | Osypka et al. | 128/783 |
| 4,722,353 | 02/1988 | Sluetz | 128/785 |
| 4,762,136 | 08/1988 | Baker, Jr. | 128/786 |
| 4,827,940 | 05/1989 | Mayer et al. | 600/375 |
| 4,830,006 | 05/1989 | Haluska et al. | 128/419 |
| 4,858,623 | 08/1989 | Bradshaw et al. | 128/785 |
| 4,876,109 | 10/1989 | Mayer et al. | 427/2 |
| 4,919,135 | 04/1990 | Phillips, Jr. et al. | 128/419 |
| 4,922,927 | 05/1990 | Fine et al. | 128/786 |
| 4,932,969 | 06/1990 | Frey et al. | 623/17 |
| 4,969,463 | 11/1990 | Dahl et al. | 128/419 |
| 4,972,848 | 11/1990 | DiDomenico et al. | 128/785 |
| 5,074,313 | 12/1991 | Dahl et al. | 128/784 |
| 5,076,272 | 12/1991 | Ferek-Petric | 128/419 |
| 5,085,218 | 02/1992 | Heil, Jr. et al. | 128/642 |
| 5,090,422 | 02/1992 | Dahl et al. | 128/784 |
| 5,139,033 | 08/1992 | Everett et al. | 128/785 |
| 5,342,407 | 08/1994 | Dahl et al. | 607/129 |
| 5,360,442 | 11/1994 | Dahl et al. | 607/129 |
| 5,385,574 | 01/1995 | Hauser et al. | 607/4 |
| 5,391,200 | 02/1995 | KenKnight et al. | 607/129 |
| 5,411,527 | 05/1995 | Alt | 607/5 |
| 5,431,649 | 07/1995 | Mulier et al. | 606/41 |
| 5,433,730 | 07/1995 | Alt | 607/5 |
| 5,480,416 | 01/1996 | Garcia et al. | 607/36 |
| 5,496,362 | 03/1996 | KenKnight et al. | 607/129 |
| 5,545,202 | 08/1996 | Dahl et al. | 607/129 |
| 5,571,162 | 11/1996 | Lin | 607/122 |
| 5,603,732 | 02/1997 | Dahl et al. | 607/129 |
| 5,681,514 | 10/1997 | Woody | 264/104 |
| 5,683,443 | 11/1997 | Munshi et al. | 607/121 |

UNITED STATES PATENT AND TRADEMARK OFFICE
CERTIFICATE OF CORRECTION

PATENT NO. : 6,501,994 B1
DATED : December 31, 2002
INVENTOR(S) : Janke et al.

It is certified that error appears in the above-identified patent and that said Letters Patent is hereby corrected as shown below:

Title page (cont'd),

| | | | |
|---|---|---|---|
| 5,683,447 | 11/1997 | Bush et al. | 607/126 |
| 5,713,926 | 02/1998 | Hauser et al. | 607/5 |
| 5,725,559 | 03/1998 | Alt et al. | 697/5 |
| 5,725,810 | 03/1998 | Brunner et al. | 261/112 |
| 5,755,764 | 05/1998 | Schroeppel | 607/122 |
| 5,759,202 | 06/1998 | Schroeppel | 607/126 |
| 5,851,227 | 12/1998 | Spehr | 607/126 |
| 5,855,594 | 01/1999 | Olive et al. | 607/28 |
| 5,871,529 | 02/1999 | Bartig et al. | 607/122 |
| 5,876,431 | 03/1999 | Spehr et al. | 607/126 |
| 5,908,447 | 06/1999 | Schroeppel et al. | 607/126 |
| 5,916,238 | 06/1999 | Hauser et al. | 607/5 |
| 5,916,243 | 06/1999 | KenKnight et al. | 607/129 |
| 5,921,979 | 07/1999 | Kovac et al. | 606/1 |
| 5,925,069 | 07/1999 | Graves et al. | 607/36 |
| 5,925,073 | 07/1999 | Chastain et al. | 607/122 --. |

FOREIGN PATENT DOCUMENTS, below "EP 0057877", insert
-- EP 0337035 10/1989 607/127
   EP 0709111 05/1996
   W0 95/08365 03/1995 --.

Signed and Sealed this

Twenty-first Day of June, 2004

JON W. DUDAS
*Director of the United States Patent and Trademark Office*